(12) United States Patent
Ashton et al.

(10) Patent No.: US 7,985,210 B2
(45) Date of Patent: Jul. 26, 2011

(54) ABSORBENT ARTICLE COMPRISING A FLAP HANDLE THAT AIDS IN THE APPLICATION OF SAID ABSORBENT ARTICLE

(75) Inventors: Gregory Ashton, Cincinnati, OH (US); Eiro Fukuda, Mason, OH (US); Ann Marie Sullivan, West Newton, MA (US); Nancy Drainville Chomyszak, West Newton, MA (US)

(73) Assignee: The Procter & Gamble Company, Cincinnati, OH (US)

( * ) Notice: Subject to any disclaimer, the term of this patent is extended or adjusted under 35 U.S.C. 154(b) by 1470 days.

(21) Appl. No.: 10/774,768

(22) Filed: Feb. 9, 2004

(65) Prior Publication Data
US 2005/0175269 A1 Aug. 11, 2005

(51) Int. Cl.
*A61F 13/15* (2006.01)
*A61F 13/20* (2006.01)

(52) U.S. Cl. .................. 604/385.01; 604/317; 604/358

(58) Field of Classification Search ............ 604/385.01, 604/389, 386–388, 358, 385.23, 385.3, 393–394, 604/385.06, 385.19; 206/438, 581
See application file for complete search history.

(56) References Cited

U.S. PATENT DOCUMENTS

| | | |
|---|---|---|
| 3,642,001 A | 2/1972 | Sabee |
| 3,810,472 A | 5/1974 | Aldinger et al. |
| 3,860,003 A | 1/1975 | Buell |
| 3,911,173 A | 10/1975 | Sprague, Jr. |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,573,986 A | 3/1986 | Minetola et al. |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,785,996 A | 11/1988 | Ziecker et al. |
| 4,795,454 A | 1/1989 | Dragoo |
| 4,834,735 A | 5/1989 | Alemany et al. |
| 4,842,666 A | 6/1989 | Werenicz |
| 4,888,231 A | 12/1989 | Angstadt |
| 4,909,803 A | 3/1990 | Aziz et al. |
| 4,988,344 A | 1/1991 | Reising |
| 4,988,345 A | 1/1991 | Reising |

(Continued)

FOREIGN PATENT DOCUMENTS
EP JP11104180 A2 * 4/1999
(Continued)

*Primary Examiner* — Leslie R Deak
*Assistant Examiner* — Susan Su
(74) *Attorney, Agent, or Firm* — Eric T. Addington; Charles R. Matson (57) ABSTRACT

A disposable absorbent article comprising a chassis comprising a liquid pervious topsheet, a liquid impervious backsheet joined with the topsheet, and an absorbent core interposed between the topsheet and backsheet; at least one sidewall adjacently disposed to the chassis; and at least one handle assisting in the application of the article onto a wearer. Preferred embodiments of the said handle include flaps, tabs, ridges, improved surface characteristics, apertures, loops, and combinations thereof. A toilet training kit comprising the article in the form of a training pant and an instruction to the caregiver for transitioning the infant to proper toilet use. A kit comprising more than one absorbent article wherein the article is positioned within said kit such that the handle is readily accessible.

18 Claims, 6 Drawing Sheets

U.S. PATENT DOCUMENTS

| | | |
|---|---|---|
| 5,006,394 A | 4/1991 | Baird |
| 5,019,065 A | 5/1991 | Scripps |
| 5,036,978 A | 8/1991 | Frank et al. |
| 5,143,679 A | 9/1992 | Weber et al. |
| 5,156,793 A | 10/1992 | Buell et al. |
| 5,163,932 A * | 11/1992 | Nomura et al. .......... 604/385.29 |
| 5,167,897 A | 12/1992 | Weber et al. |
| 5,531,732 A | 7/1996 | Wood et al. |
| 5,725,382 A * | 3/1998 | Walter et al. .................. 434/258 |
| 5,934,470 A | 8/1999 | Bauer et al. |
| 6,213,991 B1 * | 4/2001 | Kling et al. .............. 604/385.01 |
| 6,229,061 B1 * | 5/2001 | Dragoo et al. ................. 604/358 |
| 6,383,431 B1 | 5/2002 | Dobrin et al. |
| 6,443,940 B1 * | 9/2002 | Ashton et al. ................. 604/396 |
| 6,451,000 B1 | 9/2002 | Hayase et al. |
| 6,475,204 B1 * | 11/2002 | Walker .................... 604/385.06 |
| 6,478,785 B1 | 11/2002 | Ashton et al. |
| 6,626,879 B1 | 9/2003 | Ashton et al. |
| 2001/0011168 A1 | 8/2001 | Shimada et al. |
| 2002/0091368 A1 * | 7/2002 | LaVon et al. ............. 604/385.14 |
| 2002/0099353 A1 * | 7/2002 | Olson .......................... 604/389 |
| 2003/0055394 A1 | 3/2003 | Gibbs |
| 2003/0158535 A1 | 8/2003 | Dahlgren |

FOREIGN PATENT DOCUMENTS

| | | |
|---|---|---|
| EP | 1 074 235 A | 2/2001 |
| EP | 1 197 197 A | 4/2002 |
| EP | 1 205 171 A | 5/2002 |
| EP | 1 402 865 A | 3/2004 |
| GB | 2 389 300 A | 12/2003 |
| JP | 11 104180 A | 4/1999 |

* cited by examiner

Fig. 1a

PRIOR ART

ABSORBENT ARTICLE COMPRISING A FLAP HANDLE THAT AIDS IN THE APPLICATION OF SAID ABSORBENT ARTICLE

FIELD OF THE INVENTION

This invention is directed to disposable absorbent articles, such as diapers, training pants, adult incontinence articles, feminine hygiene articles and the like wherein such articles comprise a handle to assist the wearer in easy application and removal of the article.

BACKGROUND OF THE INVENTION

It has long been known that absorbent articles such as disposable diapers with fasteners, pull-on diapers, training pants, sanitary napkins, pantiliners, incontinent briefs, and the like, offer the benefit of receiving and containing urine and other bodily exudates. To effectively contain exudates, the articles must provide a snug fit around the waist and legs of the wearer. Conventional diapers generally contain a front and a rear waist section that are releasably connected by a fastening means. Application of a conventional diaper is usually performed by a caregiver with a wearer in a supine position. Such diapers allow for easy application by the caregiver but prohibit self-application by the wearer.

Disposable pull-on garments were developed, in part, to address the problem of self-application or removal. Pull-ons effectively contain exudates while allowing self-application or removal. Such garments include a waist opening, two leg openings, and a pair of side seams that are prejoined thus connecting the front and rear portions of the garment. The chassis of these garments comprises a liquid pervious bodyside liner, a liquid impervious outer cover, and an absorbent core therebetween. An additional benefit of pull-ons is that they serve as an intermediary between conventional diaper use and full toilet training. The pull-on is intended for use when a child has reached an age where he or she is ready to graduate to an underpant type garment as a replacement for disposable diapers. The pull-on provides a milestone for an infant who is developing independence from the caregiver. A suitable pull-on, however, must still provide liquid and solid absorbency while preventing waste leakage. To achieve the purpose of being a replacement for conventional diapers, a pull-on must allow the child to raise and lower the garment without the aid of a parent.

Unfortunately, current pull-on garments are not designed with child application in mind. Pull-ons are packaged in a compressed form to minimize the packaged product space, which optimizes storage and shipping costs. In its compressed state, a pull-on must be unfurled and expanded prior to application. This compression is further exacerbated by the inclusion of elastomeric material that allows the article to provide a snug fit and to contain body exudates. The inclusion of elastomeric materials requires expansion of the article prior to application. A toilet training infant, however, does not have the dexterity, strength, or coordination to fully expand the pull-on prior to application. As a result, the pull-on fails because an infant is unable to open and apply the pull-on. The impact being that the child is unable to raise or lower the pull-on without parental assistance. Even if the pull-on is opened by the child, it may be applied incorrectly such that it is not snug against the wearer's body and is improperly positioned to accept waste.

A further deficiency in current pull-on design is that it offers no grasp point optimized for an infant's hands. Parents have sufficient finger strength to apply the training pant onto a child by pinching the training pant between thumb and fingers and pulling the pant up and over the child's hips. Infants, however, do not have such finger dexterity, strength, or coordination to grasp and pull the pant up and over their own hips. When attempting to self-apply a pull-on, the infant is often either unable to apply the pant or the pant is not pulled high enough onto the infant's waist to provide effective waste absorption and control. Again, the pull-on fails because the child is unable to raise or lower the pull-on without parental assistance.

Furthermore, current pull-ons provide no grasp point for caregivers to perform a finishing adjustment. This finishing adjustment, or "finish," refers to a final adjustment of the absorbent article to ensure a proper and snug fit. Often, the finish is performed by the caregiver to ensure that the infant has applied the pull-on correctly. Infants often have problems drawing the waistband of the pull-on up and over their buttocks and need the assistance of a caregiver. In such a case, the caregiver has difficulty grasping the pull-on which may have been twisted or bunched by the infant. Furthermore, grasping a partially applied pull-on often leads to uncomfortable chafing, binding, and pinching of the infant.

Therefore, in light of the prior attempts to develop a pull-on, the present invention relates to a pull-on garment having a handle to aid in the application of the garment by either a wearer or a caregiver.

SUMMARY OF THE INVENTION

In response to the difficulties and problems described herebefore, new disposable absorbent articles have been developed that are capable of being applied or removed by a wearer without caregiver assistance and that aid in caregiver application. The present invention is directed to a disposable absorbent article comprising a chassis comprising a liquid pervious topsheet, a liquid impervious backsheet joined with the topsheet, and an absorbent core interposed between the topsheet and backsheet; at least one sidewall adjacently affixed to the chassis; and at least one handle for assisting in the application of the article onto a wearer. A variety of embodiments for the handle may be employed and combined to provide the ease of application offered by this invention including flaps, tabs, ridges, distinct grippable surfaces, apertures, loops, and combinations thereof. Another embodiment of the present inventions involves the use of a kit designed to aid a toilet training regimen. The kit comprises the aforementioned absorbent article in the form of a training pant and an instruction to the caregiver for transitioning the infant to proper toilet use.

BRIEF DESCRIPTION OF THE DRAWINGS

FIG. 4b is a cross sectional view of a handle as a ridge comprising an insert interposed between two layers taken along the sectional line 44 of FIG. 4a.

FIG. 4c is a cross sectional view of a handle as a ridge comprising an insert interposed between one layer taken along the sectional line 44 of FIG. 4a.

FIG. 4d is a cross sectional view of a handle as a ridge comprising a cap along the waist edge of the absorbent article taken along the sectional line 44 of FIG. 4a.

DETAILED DESCRIPTION OF THE INVENTION

As used herein, the term "absorbent article" or "article" refers to wearable devices, which absorb and/or contain liquid, and more specifically, refers to devices, which are placed against or in proximity to the body of the wearer to absorb and contain the various exudates discharged from the body. Suitable examples include diapers, training pants, pull-on garments, adult incontinence products and feminine care products such as sanitary napkins. Furthermore, "absorbent article" includes "disposable absorbent article" which are intended to be discarded and not laundered or otherwise restored after no more than ten uses, preferably after no more than five uses, and most preferably after a single use (although certain components may be recycled, reused, or composted).

As used herein, the term "diaper" refers to an absorbent article generally worn by infants and incontinent persons about the lower torso. Conventional diapers generally prohibit self-application by a wearer.

As used herein, the term "pull-on" or "pull-on garment" refers to a type of absorbent article worn by infants and other incontinent individuals to absorb and contain bodily exudates and are characterized by being pulled onto the body of the wearer by inserting the wearer's legs into the leg openings and pulling the article up to a point of ideal fit.

As used herein, the term "training pant" refers to a type pull-on garment worn by an infant or other incontinent individual during a toilet training regimen.

As used herein, the term "application" or "apply" refers to the process of donning the absorbent article on to a wearer by either the wearer or a caregiver.

As used herein, the term "self-application" or "self-apply" refers to the process of donning the absorbent article on to a wearer by the wearer.

As used herein, the term "finishing adjustment" or "finish," when used in reference to applying the absorbent article, refers to a final adjustment of the absorbent article to ensure a proper (i.e., the article is not creased, pinched, inverted, twisted, etc.) and snug fit. Often, although not exclusively, the finish is performed by the caregiver. The finish can include drawing the belt zone of the absorbent article over the wearer's buttocks and to the wearer's waist.

As used herein, the term "longitudinal" generally means a direction running parallel to the maximum linear dimension, typically the longitudinal axis, of the article and includes directions within 45° of the longitudinal direction.

As used herein, the term "length" of the article or component thereof generally refers to the size/distance of the maximum linear dimension, or typically to the size/distance of the longitudinal axis, or an article or part thereof.

As used herein, the terms "lateral" or "transverse" refer to a direction generally orthogonal to the longitudinal direction (e.g., in the same plane of the majority of the article and the longitudinal axis) and running parallel to the minimum linear dimension, typically the transverse axis.

As used herein, the term "width" of the article or of a component thereof refers to the to the distance/size of the dimension parallel to the transverse axis of the article or component and typically orthogonal to the longitudinal direction of the article or component thereof (e.g., orthogonal to the length of the article or component thereof).

As used herein, the term "attached" encompasses configurations whereby an element is directly secured to another element by affixing the element directly to the other element.

As used herein, the term "joined" or "connected" encompasses configurations whereby an element is directly secured to another element by affixing the element directly to the other element and configurations whereby an element is indirectly secured to another element by affixing the element to intermediate member(s), which in turn are affixed to the other element.

As used herein, "along the longitudinal axis" means at least partially parallel to the longitudinal axis.

While not being limited to any one particular absorbent article embodiment, a pull-on garment is particular preferred. Many forms of pull-on garments exist beyond the conventional embodiments characterized below. For example, pull-ons may use elastic elements secured in an elastically contractible condition in the waist and leg openings to allow gathering at the elasticized portions and blousing in the non-elasticized portions.

Figure 1A:
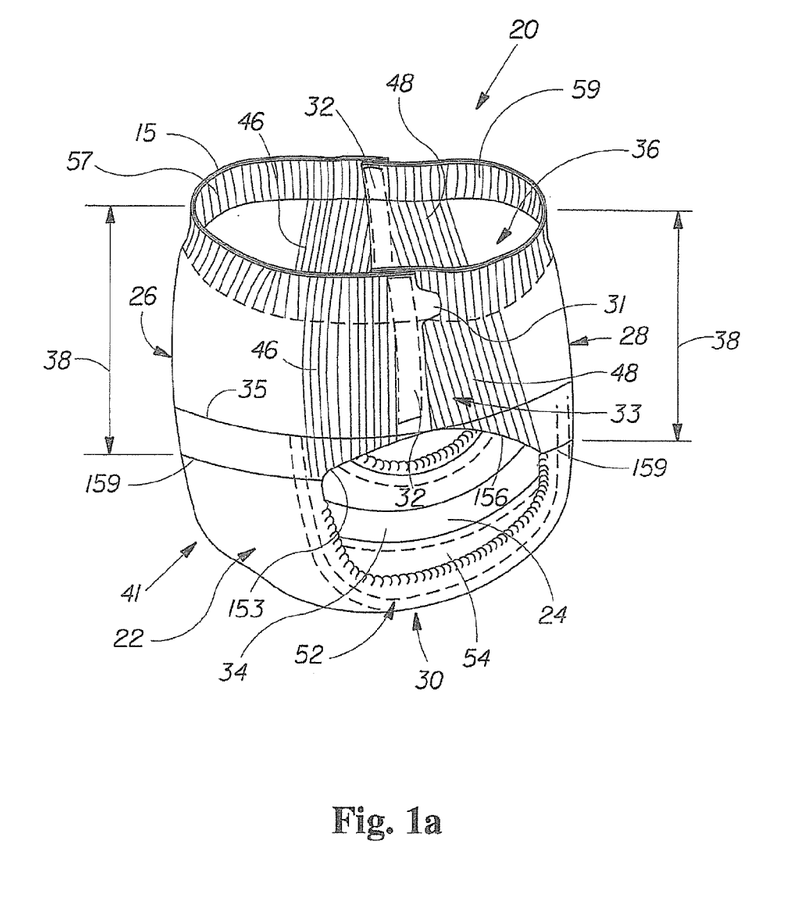
FIG. 1*a* is a perspective view of an absorbent article.
Figure 1B:
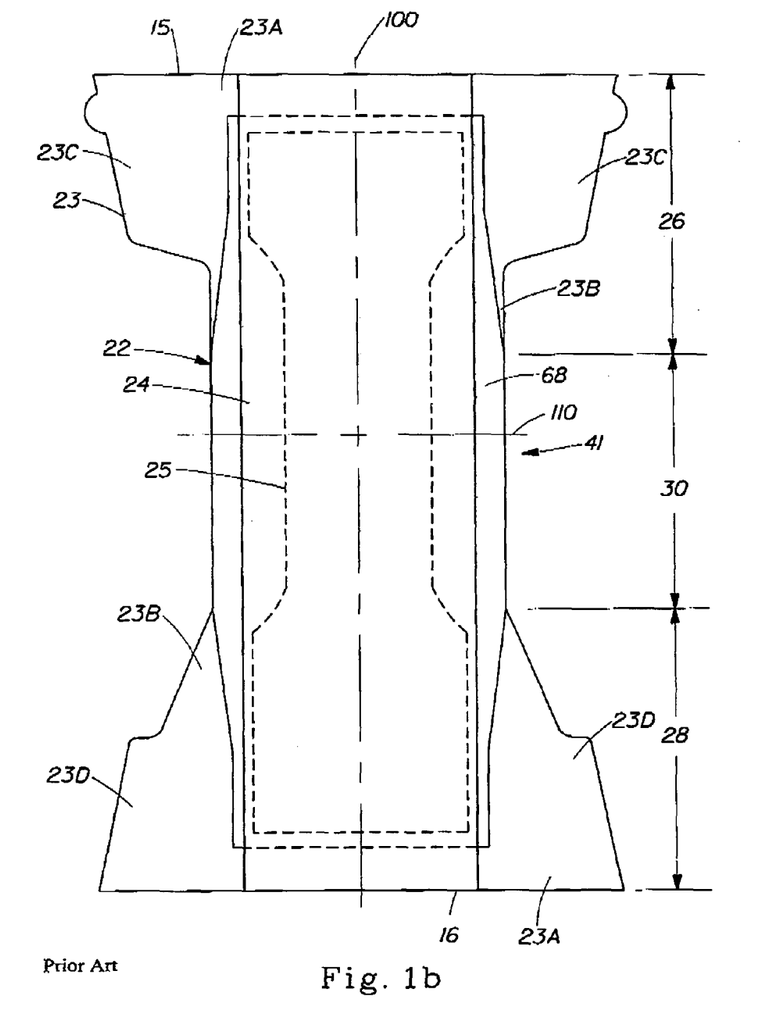
FIG. 1*b* is a plan view of an absorbent article.

FIGS. 1a and 1b illustrate a conventional pull-on diaper 20 known in the art. The pull-on 20 has the front region 26, the back region 28 and the crotch region 30 between the front region 26 and the back region 28. The pull-on 20 also has two centerlines; a longitudinal axis 100 and a transverse axis 110. The pull-on 20 and component materials thereof also have a wearer-facing surface which faces the skin of wearer in use and a garment-facing surface which is the opposite surface to the body-facing surface.

The pull-on 20 primarily comprises a chassis 41, a waist elastomeric material (not shown), a side elastomeric material (not shown), and at least one sidewall 33. The sidewall 33 is the region of the pull-on 20 interconnecting the front region 26 and the back region 28, and further defines a portion of the leg edge 153, 156 and at least a portion of the waist edge 15, 16. The sidewall 33 may be constructed in a variety ways including extensible or nonextensible ears (i.e., unitary portion(s) extending from the chassis) and discrete extensible or nonextensible panel(s) affixed to the pull-on. The pull-on may further have elasticized leg cuffs 52 including inner barrier cuffs 54. The side elastomeric material forms extensible ears 46 and 48. The waist elastomeric material forms an extensible waistband 57 and 59. The side elastomeric material and the waist elastomeric material may be separate elements to each other and disposed so as not to overlap to each other in the longitudinal direction of the pull-on 20. This allows more independent behavior of the waist and side elastomeric materials to allow for adjustments in dimension extension, pressure, etc. The extensible ears 46, 48 and continuous extensible waistband 57, 59 are extensible at least in the lateral direction.

The extensible ears 46, 48 are joined at the seams 32 to connect the front region 26 to the back region 28 and to create one waist opening 36 defined by a waist edge 15, 16 and two leg openings 34. In this preferred embodiment, the extensible ears 46, 48 and the seams 32 collectively form the sidewall 33. The welding of the seams 32 can be performed by any suitable means known in the art appropriate for the specific materials employed in the extensible ears 46 and 48. Thus, sonic sealing, heat sealing, pressure bonding, adhesive or cohesive bonding, sewing, autogeneous bonding, and the like may be appropriate techniques. Preferably, the extensible ears 46, 48 are joined by a predetermined pattern of heat/pressure or ultrasonic welds which withstands the forces and stresses generated on the pull-on diaper 20 during wear. The pull-on 20 may have tear open tabs 31, whose positioning is associated with the seams 32. In an alternative embodiment, not shown in the figures, the seams 32 may include a resealable fastener, such as but not limited to, hook and loop fasteners, buttons, zippers, tab and slot, adhesives, co-adhesives and the like. While the seams 32 are shown located at the approximate mid-point of the opposing extensible ears 46, 48, nothing in this present invention limits the seams 32 to only this location.

The pull-on 20 further comprises a continuous waist edge 15, 16 along the periphery of the waist opening 36. Further, a continuous belt zone 38 extends circumferentially about the pull-on 20. The belt zone is the portion of the pull-on defined by the waist edge 15, 16; a leg edge 153, 156; and a lateral edge 159 of the crotch region 30 in the front region 26 and the back region 28.

The chassis 41, referring to FIG. 1b, comprises an absorbent core 25 and a plurality of layers disposed in association with the absorbent core 25, such as a topsheet 24 and a backsheet 22 associated with the topsheet 24. The absorbent core 25 is disposed between the topsheet 24 and the backsheet 22. The chassis 41 further may include one or more additional layers associatedly disposed with the absorbent core 25. The topsheet 24 has a body-facing surface which is positioned adjacent to the wearer's body during use. The backsheet 22 has an outer-facing surface which is positioned away from the wearer's body. Preferably, the backsheet 22 comprises an inner barrier film 68 and a nonwoven outer cover 23. While the topsheet 24, the backsheet 22, and the absorbent core 25 may be assembled in a variety of well known configurations, exemplary chassis configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

Preferably, the nonwoven outer cover 23 covers almost all of the area of the outermost portion of the pull-on 20. The nonwoven outer cover 23 may have generally the same shape as the pull-on 20. The nonwoven outer cover 23 has waist end portions 23A and side portions 23B. The nonwoven outer cover 23 also has a side extended portion 23C in the front region 26 and a side extended portion 23D in the back region 28. Alternatively, the nonwoven outer cover 23 may be eliminated, and the inner barrier film 68 may have generally the same shape as the pull-on 20.

The absorbent core 25 may be any absorbent member which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may comprise one or more layers or structures). Further, the size and absorbent capacity of the absorbent core 25 may also be varied to accommodate wearers ranging from infants through adults. The total absorbent capacity of the absorbent core 25 should be compatible with the design loading and the intended use of the pull-on 20.

The absorbent core 25 in a preferred embodiment may be an asymmetric, modified hourglass-shape having ears in the front and back waist regions 26 and 28. Other exemplary absorbent structures for use as the absorbent core 25 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

The absorbent core 25 may include other optional components. One such optional component is the core wrap (not shown), i.e., a material, typically but not always a nonwoven material, which either partially or totally surrounds the core. Suitable core wrap materials include, but are not limited to, cellulose, hydrophilically modified nonwoven materials, perforated films and combinations thereof.

The topsheet 24 is preferably compliant, soft feeling, and non-irritating to the wearer's skin. Further, the topsheet 24 is liquid pervious thereby permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 25 (i.e., to prevent rewet). If the topsheet 24 is made of a hydrophobic material, it is preferable that at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 25. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991.

In preferred embodiments, the topsheet 24 is a nonwoven web that can provide reduced tendency for surface wetness and consequently facilitate maintaining urine absorbed by the absorbent core 25 away from the user's skin, after wetting. One of the preferred topsheet materials is a thermobonded carded web which is available as Code No. P-8 from Fiberweb North America, Inc. (Simpsonville, S.C., U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. Yet another preferred topsheet material is a thermobonded carded web which is available as Code No. Profleece Style 040018007 from Amoco Fabrics, Inc. (Gronau, Germany).

Another preferred topsheet 24 comprises an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries," which issued to Thompson on Dec. 30, 1975; U.S. Pat. No. 4,324,246 entitled "Disposable Absorbent Article Having A Stain Resistant Topsheet," which issued to Mullane, et al. on Apr. 13, 1982; U.S. Pat. No. 4,342,314 entitled "Resilient Plastic Web Exhibiting Fiber-Like Properties," which issued to Radel et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression," which issued to Ahr et al. on Jul. 31, 1984; and U.S. Pat. No. 5,006,394 "Multilayer Polymeric Film" issued to Baird on Apr. 9, 1991.

The backsheet 22 preferably comprises a inner barrier film 68 and a nonwoven outer cover 23. The inner barrier film 68 is preferably impervious to liquids (e.g., urine) and is preferably manufactured from a thin plastic film. The inner barrier film 68 has a body-facing surface and an outer-facing surface. More preferably, the plastic film permits vapors to escape from the pull-on 20. In a preferred embodiment, a microporous polyethylene film is used for the inner barrier film 68. A suitable microporous polyethylene film is manufactured by Mitsui Toatsu Chemicals, Inc., Nagoya, Japan and marketed in the trade as Espoir No. The backsheet 22 is preferably compatible with ventilation and side seaming design/process.

A suitable plastic film material for the inner barrier film 68 is a thermoplastic film having a thickness of from about 0.012 mm (0.5 mil) to about 0.051 mm (2.0 mils), preferably comprising polyethylene or polypropylene. Preferably, the plastic film has a basis weight of from about 5 g/m$^2$ to about 35 g/m$^2$. Other flexible liquid impervious materials, however, may be used. Herein "flexible" refers to materials which are compliant and which will readily conform to the general shape and contours of the wearer's body.

The nonwoven outer cover 23 is joined with the garment-facing surface of the inner barrier film 68 to form a laminate (i.e., the backsheet 22). The nonwoven outer cover 23 is positioned as the outermost lamina of the pull-on 20 and covers at least a portion of the outermost portion of the pull-on 20. The nonwoven outer cover 23 may be joined to the inner barrier film 68 by any suitable attachment means known in the art. For example, the nonwoven outer cover 23 may be secured to the inner barrier film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H. B. Fuller Japan Co., Ltd., Osaka, Japan as JM-6064.

In a preferred embodiment, the nonwoven outer cover 23 is a carded nonwoven web, for example, obtainable from Havix Co., LTD., Gifu, Japan as E-2341. The nonwoven outer cover 23 is made of bi-component fibers of a polyethylene (PE) and a polyethylene terephthalate (PET). The ratio of PE/PET is about 40/60. The PE/PET bi-component fiber has the dimension of 2 decitex×51 mm. Another preferred carded nonwoven web is obtainable from Chisso Corp., Osaka, Japan. The nonwoven outer cover 23 may also be made of bi-component fibers of a polyethylene (PE) and a polyethylene terephthalate (PET). The ratio of PE/PET is about 30/70.

In another preferred embodiment, the nonwoven web is a spunbonded nonwoven web, for example, obtainable from Mitsui Petrochemical Industries, Ltd., Tokyo, Japan. The nonwoven web is made of bi-component fibers consisting of a polyethylene (PE) sheath and a polypropylene (PP) core. The ratio of PE/PP is about 80/20. The PE/PP bi-component fiber has the thickness of approximately 2.3 decitex.

The backsheet 22 is preferably positioned adjacent the outer-facing surface of the absorbent core 25 and is preferably joined thereto by any suitable attachment means known in the art. For example, the backsheet 22 may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art. In an alternative embodiment, the absorbent core 25 is not joined to the backsheet 22 and/or the topsheet 24 in order to provide greater extensibility in the front region 26 and the back region 28.

The elasticized leg cuffs 52 provide improved containment of liquids and other body exudates. The elasticized leg cuffs 52 may comprise several different embodiments for reducing the leakage of body exudates in the leg regions. (The leg cuffs can be and are sometimes referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (or gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (or barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

While each elasticized leg cuff 52 may be configured so as to be similar to any of the leg bands, side flaps, barrier cuffs, or elastic cuffs described above, it is preferred that each elasticized leg cuff 52 comprises inner barrier cuffs 54 each comprising a barrier flap and a spacing means as described in the above-referenced U.S. Pat. No. 4,909,803. The inner barrier cuffs 54 may have an insert element which is highly impermeable, but preferably breathable. In a preferred embodiment, the elasticized leg cuff 52 additionally comprises an elastic gasketing cuff with one or more elastic strands, positioned outboard of the barrier cuff 54 such as described in the above-referred U.S. Pat. Nos. 4,695,278 and 4,795,454. The elastic strands may be prestrained, before being joined, up to between 30% and 200%, preferably between 50% and 150%. A preferred elastic strand is manufactured by Fulflex International Company under the designation 9312.

The pull-on diaper 20 has the front extensible ear 46 and the back extensible ear 48. The extensible ear 46 and 48 preferably comprises a stretch laminate. A preferred stretch laminate is described in more detail in U.S. Pat. No. 6,478,785 issued to Ashton et al. on Nov. 12, 2002. Preferably at least one of the front and back extensible ears 46 and 48 is elastically extensible in at least the lateral direction. More preferably, both the front and the back extensible ears 46 and 48 are elastically extensible in at least the lateral direction. In an alternative embodiment, the front and back extensible ear 46 and 48 is elastically extensible both in the lateral and longitudinal directions. Herein "elastically extensible" refers to materials that are capable of extending in at least one direction to a certain degree without undue rupture and that have the ability to return to approximately their original dimensions after the force that extended the material is removed.

The extensible ear 46 and 48 may be formed by unitary elements of the pull-on diaper 20 (i.e., they are not separately manipulative elements secured to the pull-on diaper 20, but rather are formed from and are extended portions of one or more of the various layers of the pull-on diaper). In a preferred embodiment, the extensible ear 46 and 48 is a projected member of the chassis 41. Preferably, the extensible ear 46 and 48 comprises at least one unitary element or a continuous sheet material that forms a part of the chassis 41 and continuously extends to the extensible ear 46 and 48 (e.g., the nonwoven outer cover 23). Alternatively, the extensible ear 46 and 48 may be discrete members which do not have common unitary elements with the chassis 41. The extensible ear 46 and 48 would thus be joined to the side portions of the chassis 41. Furthermore, the pull-on diaper 20 may comprise a single extensible ear (not shown) that may be a unitary element or a separately manipulative element of the pull-on diaper. The single extensible ear would connect the front region 26 to the back region 28 with the seam 32 being the weld point of the ear to the chassis. The single extensible ear would project from or be attached to the front region 26 or the back region 28 and would be attached to opposing region by way of the seam 32.

The pull-on diaper 20 has at least one handle for assisting in the application of the article onto a wearer or removal of the article from a wearer. The handle is designed to withstand the forces necessary to apply or remove the pull-on diaper 20 including insertion of the wearer's feet through the leg openings, elevating the pull-on up the wearer's legs and over the wearer's buttocks, achieving an ideal snug fit, and lowering the pull-on 20.

The handle embodiments, described in greater further detail below, are generally not limited in location or number. Most embodiments show the handle presented as a pair; however, the invention clearly includes handles appearing singularly and in numbers greater than two. Furthermore, in the embodiments comprising more than one handle, the handles may be placed symmetrically or non-symmetrically. It must be further emphasized that locations of the handles in the embodiments listed below are not to be read as limiting. Handle placement may occur anywhere such that the handle may be engaged by the wearer.

Figure 2A:
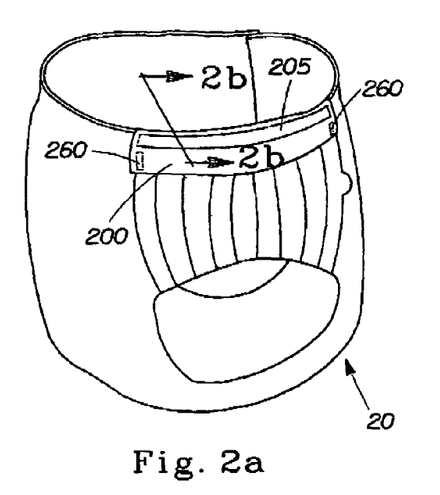
FIG. 2*a* is a perspective view of an absorbent article of the present invention having the handle as a flap.

FIG. 2*a* shows a perspective view of one embodiment of the handle as a flap 200 extending from the chassis or sidewall. The flap 200 is, generally, a stratum disposed adjacent to the chassis 41 or sidewall 33 such that, during application or removal, the fingers of the wearer or caregiver may be inserted under, into, or through a gap 210 formed between the chassis 42 or sidewall 33 and said stratum. While not limited in theory, the flap 200 allows the individual applying or removing the pull-on 20 to cup the flap between the fingers and palm or encircle the flap by fingers and thumb.

In this preferred embodiment, the flap 200 is located longitudinally at or within the belt zone and laterally spans the width of the sidewall. The flap 200 may either be of unitary or multiple construction as represented in the cross sectional views (taken along sectional line 2-2 of FIG. 2*a*) of the flap in FIG. 2*b* and FIG. 2*c*, respectively. Optionally, the sidewall may comprise a single extensible ear.

Figure 2B:
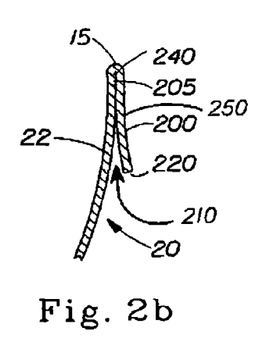
FIG. 2*b* is a cross sectional view of a handle as a flap comprising a unitary construction taken along the sectional line 2-2 of FIG. 2*a*.

The unitary construction of FIG. 2*b* entails a stratum 250 of the material, either a lamina or laminate, comprising the belt zone extending beyond the waist edge 15, 16 that is folded radially away from the wearer-facing surface and welded. The resulting flap 200 should form a gap 210 of an effective length such that a wearer may, easily engage the flap with his or her fingers. The effective length is the length of the flap 200 measured on the garment-facing surface from the waist edge 15 to the lower end 220 of the flap 200. Ideally, the effective length should be from about 10 mm to about 50 mm. Most preferably, the effective length is from about 20 mm to about 30 mm. Preferably, the flap 200 is welded to the backsheet 22 of the pull-on 20 in order to keep the flap snug against the backsheet 22 when the flap 200 is not engaged by the wearer. Furthermore, the weld prevents the flap 200 from unfolding; thus, preserving the integrity of the handle. The flap 200 may have a lateral weld 205, which runs substantially laterally along the pull-on 20 and is generally in proximity to the waist edge 15, and/or a longitudinal weld 260, which runs substantially longitudinally along the pull-on 20 and are generally in proximity to the distal longitudinal edges of the flap 200. If a lateral weld is absent, the flap 200 may be cut along the waist edge 15 and through to the hingepoint 240. The cut may extend over the complete lateral width of the flap 200 or a portion of the lateral width of the flap 200. The cut should have sufficient width to allow penetration of the wearer's fingers so that the flap 200 may be encircled by the wearer's hand. The cut may further extend over a portion of the flap 200 to yield a shaped handle.

Figure 2C:
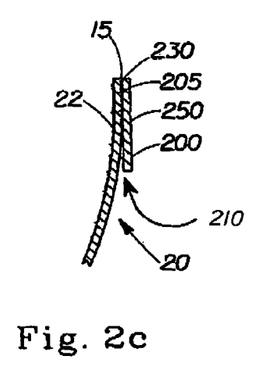
FIG. 2*c* is a cross sectional view of a handle as a flap comprising a multiple layer construction taken along the sectional line 2-2 of FIG. 2*a*.
Figure 2D:
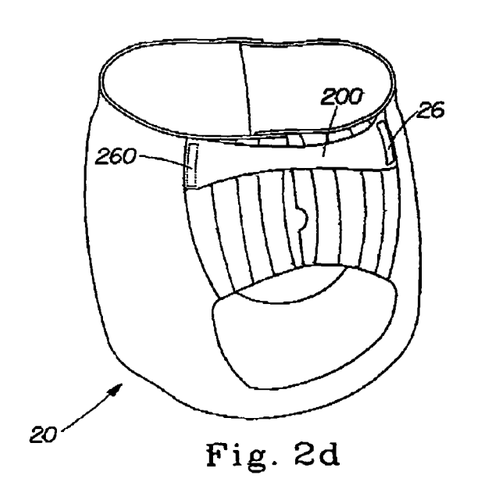
FIG. 2*d* is a perspective view of an absorbent article of the present invention having the handle as a flap.

The multiple construction of FIG. 2c entails a discrete stratum 250 that is welded to the garment-facing surface of the backsheet 22 at a connection point 230. The connection point 230 is the location on the pull-on diaper 20 where the flap is welded. The connection point 230, as shown in FIG. 2c, is ideally located adjacent to the waist edge 15. The connection point 230 may exist anywhere on the pull-on diaper 20 limited only such that the flap may be engaged by the wearer. The connection point 230 may also be on the wearer-facing surface of the pull-on diaper 20 with the resulting flap 200 extending over the waist edge and away from the garment-facing surface of the backsheet 22. The flap 200 should form a gap 210 of an effective length, as described above, such that a wearer can easily engage the flap 200 with his or her fingers. Ideally, the effective length should be from about 10 mm to about 50 mm. Most preferably, the effective length is from about 20 mm to about 30 mm. The flap 200 is welded to the pull-on 20 in order to keep the flap snug against the garment-facing surface of the backsheet when the flap 200 is not engaged by the wearer and to prevent the flap 200 from unfolding during use. The flap 200 may have a lateral weld 205, which runs substantially laterally along the pull-on 20 and is generally in proximity to the waist edge 15, and/or a longitudinal weld 260, which runs substantially longitudinally along the pull-on 20 and are generally in proximity to the distal longitudinal edges of the flap 200. If no lateral weld 205 exists, the flap 200 should be constructed so that the flap 200 may be encircled by the wearer's hand. Ideally, if no lateral weld 205 exists, the flap 200 may be of a substantially hyperbolic shape as shown in FIG. 2d.

The flap 200 may be welded by an adhesive, heat bonds, pressure bonds, ultrasonic bonds, dynamic mechanical bonds, or combinations thereof.

Alternately, the flap 200 may be located at any place in the absorbent article such that the flap may be engaged by the wearer. The dimensions and shape of the flap 200 are limited only such that the article maintains a comfortable fit and the flap 200 does not interfere with the application of other outer garments (i.e., pants, gown). The flap 200 is not limited in width and may span any portion of the absorbent article up to circumscribing the entire article. The flap 200 may be constructed from a variety of materials well known in the art such as wovens, nonwovens, foams, and polymeric materials.

In a particularly preferred embodiment, the handle is a flap of multiple construction. The flap is a discrete stretch laminate comprising an elastic film layer bonded to a nonwoven layer. The elastic film layer is preferably a film available from Tredegar Film Products of Richmond, Va. under the designation X25007. The nonwoven layer is preferably a nonwoven available from BBA Nonwovens of Nashville, Tenn. under the designation "Highly Elongatable Carded Nonwoven." The elastic film layer and the nonwoven layer are intermittently bonded or continuously bonded. Preferably, the layers are continuously bonded to one another by use of an adhesive. The adhesive is preferably an adhesive available from Ato Findley of Milwaukee, Wis. under the designation H2031. The adhesive is preferably applied in a spiral pattern as illustrated in U.S. Pat. No. 3,991,173 to Sprague, Jr., at a basis weight of about 0.116 g/m$^3$. Alternatively, the layers may be bonded by heat bonding, ultrasonic bonding, pressure bonding, dynamic mechanical bonding, or any other method known in the art.

In this particularly preferred embodiment, the stretch laminate is preferably a "zero strain" stretch laminate. A zero strain stretch laminate is a laminate comprised of at least two layers which are bonded to one another along at least a portion of their coextensive surfaces while in a substantially untensioned ("zero strain") condition. The resulting zero strain stretch laminate is thereby rendered elastically extensible by mechanical stretching or ring-rolling. Particularly preferred methods and apparatus used for making stretch laminates utilize meshing corrugated rolls or plates to mechanically stretch the components. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; U.S. Pat. No. 5,143,679 issued to Weber et al. on Sep. 1, 1992. The stretch laminate preferably exhibits stretchability in at least the lateral direction. The laminate preferably exhibits stretchability from about 5% to about 200% when subjected to pull forces of up to 2 kgf. Most preferably the stretch laminate exhibits stretchability from about 50% to about 100%.

In this particularly preferred embodiment, the flap is welded to the pull-on both laterally and longitudinally. The lateral weld substantially spans the width of the uppermost edge of the flap and is adjacent to the waist edge. The longitudinal welds substantially span the longitudinal length of the distal ends of the flap. One of the longitudinal welds is substantially contiguous with the seam (which in this preferred embodiment is a front seam whereby a single extensible ear connects the back region to the front region). The opposing longitudinal weld is within the back region of the chassis. The welds are preferably pressure bonds but other bonding methods known in the art may also be used.

In this particularly preferred embodiment, the flap may be up to about 50 mm in length but is preferably 30 mm in length. The width of the flap is dependent upon the size of the pull-on to which the flap 200 is affixed. In this preferred embodiment, the width of the flap 200 must be great enough to span the extensible ear and a portion of the chassis within the back region.

Figure 3A:
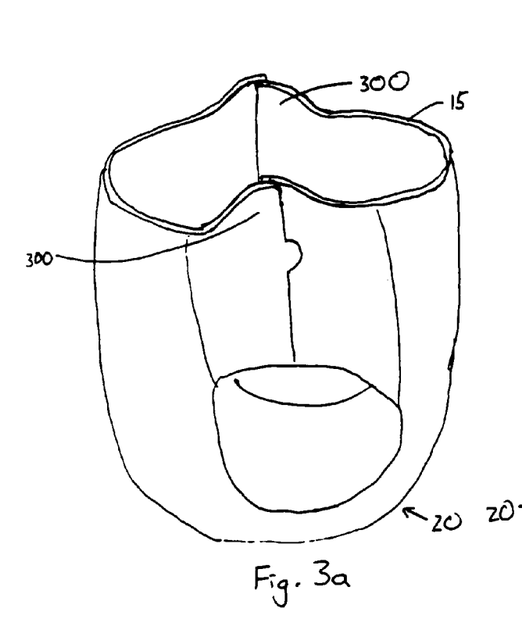
FIG. 3*a* is a perspective view of an absorbent article of the present invention having the handle as a tab.

FIG. 3a shows a perspective view of a second embodiment of a handle as a tab 300 extending from the belt zone. The tab 300 is, generally, a stratum disposed adjacent to the chassis 41 or sidewall 33 such that, during application or removal, the tab 300 is engaged by pinching the tab 300 between the fingers of the wearer or caregiver. In a preferred embodiment of FIG. 3a, the tab 300 is a unitary tongue of the material comprising the belt zone extending from the waist edge 15. The tab 300 extend such that the one dimension of the tab 300 parallels the waist edge 15. The tab 300 is shown as being laterally defined by the sidewall; however, the location and dimensions of the tab 300 are limited only by the wearer's ability to reach and engage the tab 300.

While FIG. 3a shows the preferred location of the tab 300 as extending from the waist edge 15, the tab 300 may be located anywhere in the diaper such that the wearer can engage the tab 300 while applying the diaper. The tab 300 may be positioned along the sidewall of the article, preferably as an extension of the seams 32. Furthermore, the tab 300 may be located within the garment-facing surface of the chassis.

The dimensions of the tab 300 are of an effective size such that a wearer can engage the tab 300 with his or her fingers. The maximum dimensions of the tab 300 are limited only such that the article maintains a comfortable fit and the tab 300 does not interfere with the application of other outer garments (i.e., pants, gown). Ideally, the tab had a longitudinal length of about 10 mm to about 50 mm. Most preferably, the tab has a longitudinal length of about 20 mm to about 30 mm. While not limited to a particular shape, a preferred tab 300 is substantially parabolic in shape.

Figure 3B:
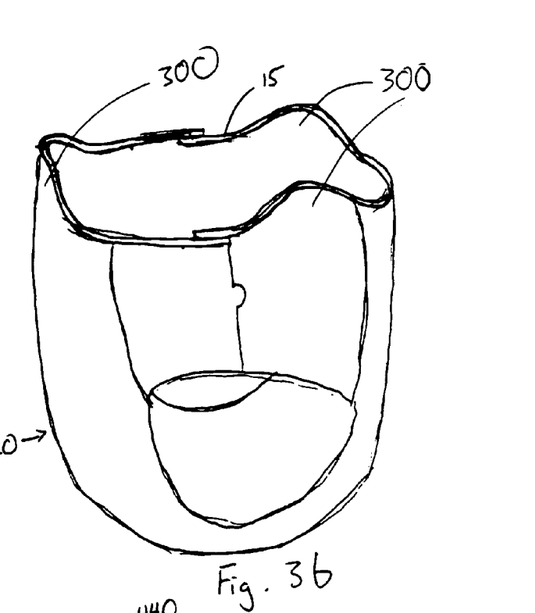
FIG. 3b is a perspective view of an absorbent article of the present invention having the handle as a tab of sinusoidal configuration.

In a preferred embodiment of FIG. 3b, the waist edge 15 is substantially sinusoidal. The pull-on diaper 20 generally will comprise multiple tabs; preferably with two tabs being in the rear region and one tab in the front region.

The tab 300 may be a discrete piece of material affixed to the pull-on diaper 20. If the tab 300 is a discrete piece of material rather than a unitary tongue of material comprising the belt zone, the tab 300 is secured to the article by any welding technique well know in the art such as by adhesive, heat bonds, pressure bonds, ultrasonic bonds, dynamic mechanical bonds, or combinations thereof. Ideally, the tab 300 will be affixed within the belt zone and in proximity to the waist edge 15, but location of the tab 300 is not limited. The tab 300 may be constructed from a variety of materials well known in the art such as wovens, nonwovens, foams, and polymeric materials.

Figure 4A:
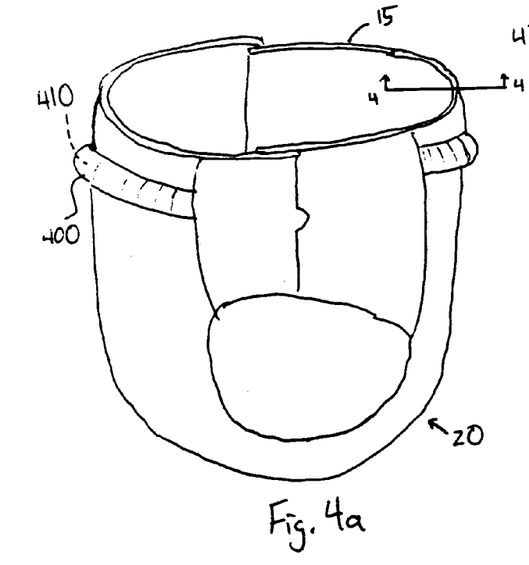
FIG. 4a is a perspective view of an absorbent article of the present invention having the handle as a ridge.

FIG. 4a shows a perspective view of a third embodiment of the handle as a ridge 400 protruding from the belt zone of the pull-on diaper 20. The ridge 400 is, generally, a protrusion extending from at least the garment-facing surface of the pull-on 20 such that the ridge provides increased caliper which may be engaged by the wearer's or caregiver's fingers. In a preferred embodiment, the ridge 400 is proximate to the waist edge 15. The ridge 400 has a minimum effective cross-dimension such that the ridge is a grippable protuberance for the wearer. The maximum effective cross-dimension of the ridge 400 is limited only such that the article maintains a comfortable fit and the ridge 400 does not substantially interfere with the application of other outer garments (i.e., prohibit self-application of pants, gown, etc.). Preferably, the ridge 400 has an effective cross-dimension of about 2 mm to about 15 mm. Most preferably, the ridge 400 has an effective cross-dimension of about 5 mm to about 8 mm. The effective cross-dimension is the difference between the maximum caliper of pull-on 20 at the ridge 400 subtracted by the minimum caliper of the pull-on 20 as measured immediately below (i.e., "below" being the downward direction of a pull-on 20 when worn) the ridge 400. Caliper, as used herein, generally refers to a linear dimension as measured orthogonal to the plane defined by the longitudinal and lateral axes.

In a preferred embodiment, the ridge 400 comprises an insert 410 interposed between at least one layer. The insert 410 may be comprised of any material well known in the art such as wovens, nonwovens, foams, and polymeric materials. The insert 410 may be in any shape and size which will create a graspable protuberance while still maintaining a comfortable and non-irritating fit. In one embodiment shown in the cross-sectional view FIG. 4b, taken along the sectional line 4-4 of FIG. 4a, the insert 410 is a cord of an open-cell foam material with a relatively semi-circular cross dimension with the rounded edge being garment-facing. The insert 410 is shown interposed between two layers, an inner layer 420 and outer layer 430. A layer can be any single lamina or combination of laminae (i.e., a laminate) typically used in construction of the pull-on 20. Preferably, the cord spans the front and rear region of the pull-on and is interposed between the outer layer 430 comprising the outer nonwoven cover and the inner layer 420 comprising the inner barrier film. The layers may be welded together at the contact points 440 immediately adjacent to the insert 410. Optionally, the insert 410 itself may be welded to one or more layers. This welding secures the insert 410 in place and prevents it from shifting within the interstice of the layers. In another embodiment (not shown), the insert is interposed between the inner layer or outer layer of the pull-on diaper and a discrete patch comprised of a lamina or laminate. The patch may be welded to the layer at the contact points immediately adjacent the insert.

Figures 4B, 4C, 4D:
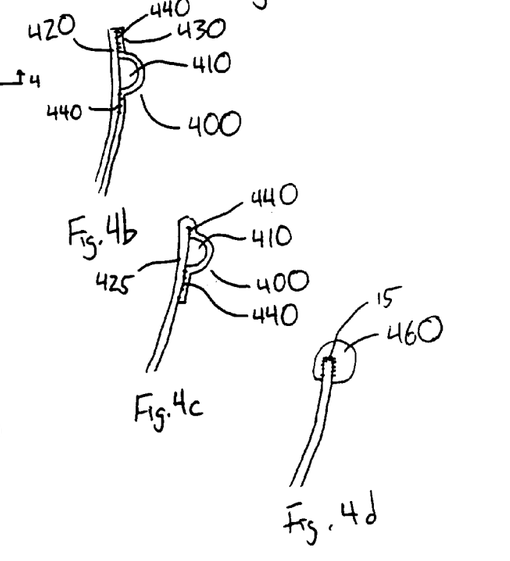

Furthermore, in another embodiment shown in the cross-sectional view FIG. 4c (taken along the sectional line 4-4 of FIG. 4a), the insert 410 may be interposed between a single layer 425, either a lamina or laminate that is folded around the insert 410. In such a configuration, the single lamina or the laminate is welded to itself at contact points 440 immediately adjacent to the insert; thus, sealing the insert 410 in place. It should be noted that a single contact point may exist especially if the insert 410 is disposed immediately adjacent to the waist edge 15. Conversely, the insert 410 may be affixed to the backsheet 22 of the pull-on diaper 20 without overlapping patch 450.

FIG. 4d illustrates a cross-sectional view, as taken along the sectional line 4-4 of FIG. 4a, of the ridge 400 as a cap 460 along the waist edge 15 of the pull-on 20. The cap 460 ideally comprises a foam material but a variety of wovens, nonwovens, and polymerics may also be utilized. The cap 460, as shown, is affixed along the waist edge 15, the garment-facing surface immediately adjacent the waist edge 15, the wearer-facing surface immediately adjacent the waist edge 15, and combinations thereof and therebetween. Another embodiment involves the ridge 400 being formed by folding or rolling a portion of the material comprising the belt zone to provide a palpably raised surface. The interface between the pull-on and the resulting fold is welded to prevent the fold from unraveling during use.

The affixation and welding of any of the ridge 400 embodiments may be performed by any welding technique well know in the art such as by adhesive, heat bonds, pressure bonds, ultrasonic bonds, dynamic mechanical bonds, or combinations thereof. Furthermore, the ridge 400 may fully, partially, or intermittently circumscribe the article. While partially circumferential peripheral ridges are illustrated, the ridge 400 will serve the same functional purpose even where fully or intermittently circumscribing the article.

Figures 5A, 5B:
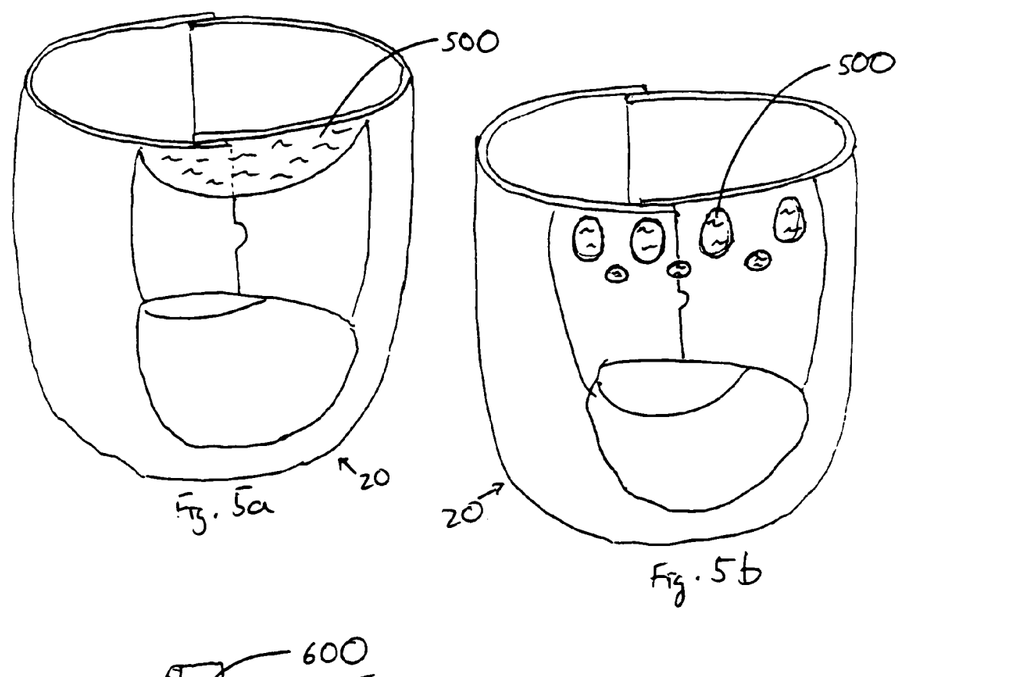
FIGS. 5a and 5b are perspective views of an absorbent article of the present invention having the handle as a region with an improved grippable surface.

FIG. 5a is a perspective view of another embodiment of the handle as a region 500 within the absorbent article with a distinct grippable surface characteristic. A region 500 with a distinct grippable surface characteristic refers to a palpable difference in texture, pliancy, tackiness, or friction of the region compared to the surface immediately adjacent the region. Most preferably, the distinct grippable surface characteristic is an increase in friction. The distinct grippable surface characteristic can be imparted to the region 500 by a variety of methods. The outer-most surface of the pull-on (e.g., typically the nonwoven outer cover) generally has a coefficient of static friction from about 0.15 to about 0.23. Coefficient of static friction values at these relatively low levels facilitate application of garments over the pull-on diaper 22. The region may have a distinct grippable surface exhibiting a coefficient of static friction from greater than about 0.3 to less than about 4.0, preferably from about 0.4 to about 2.0, and most preferably from about 0.7 to about 1.5. The coefficient of static friction is measured according to the test method disclosed in U.S. Pat. No. 6,626,879 entitled "Disposable Absorbent Article Having Article Retention Zones" issues to Ashton et al. on Sep. 20, 2003.

In one embodiment, the characteristic can be imparted to the region by lamination with one or more laminae that exhibit a distinct grippable surface characteristic. The region is preferably laminated by coating or patches. When the region is laminated by coating, a suitable coating composition is used to increase the coefficient of friction including, but not limited to, coatings of pressure-sensitive materials or of tacky materials. Suitable coatings include ethylene vinyl acetate copolymers, polyvinyl acetate, styrene-butadiene, cellulose acetate butyrate, ethyl cellulose, acrylics, synthetic rubber hot melt, and other hot melts. Methods for coating include, but are not limited to, extrusion, coating, slot coating, gravure printing, and screen printing. When the region is laminated by patches, the patches can be made from a number of different materials that are thin, flexible, and that can be affixed to the region. Examples of materials from which such patches can be made are polymeric films, apertured films, fibrous nonwoven sheets, scrims, scrim nettings, or fibrous flocked substrates. The patches may be affixed to the region by affixation means well known in the art with preference toward heat/pressure affixation. A more detailed discussion of lamination by coating or patches is contained in above-referred U.S. Pat. No. 6,626,879, particularly the disclosure on retention zones.

In one embodiment, the characteristic can be imparted to the region by constructing the region from a material that inherently exhibits the characteristic. Preferably, an open cell foam may be used to provide a sidewall with the abovementioned coefficient of static friction; however, a variety of nonwoven, woven, polymeric, and foam materials exist exhibiting sufficient coefficient of static friction so as to assist the grasping of the article. Additionally, the characteristic can be imparted to the region by mechanical or chemical processing.

Additional surface characteristics of the region instead of and in addition to an increased friction coefficient. The region can exhibit a texture such that the material comprising the region has a palpable quality. For example, texture can be imparted mechanically by ring rolling the region. An exemplary method of ring rolling is illustrated in U.S. Pat. No. 6,383,431 issued May 7, 2002 to Dobrin et al. The region can exhibit a pliancy such that the material comprising the region yields to touch. The region can exhibit a tackiness such that the material comprising the region has a slightly adhesive or gummy feel to the touch.

Alternately, the region may be located anywhere on the pull-on and is not limited to the sidewall. The region need only be located such that the region may be grasped by the wearer. Furthermore, the region is not limited in dimension and may span any portion of the absorbent article up to circumscribing the entire article. The region may be of a may circumscribe the pull-on diaper 20, partially circumscribe the pull-on diaper 20 as seen in FIG. 5*a*, and or comprise numerous discrete areas as seen in FIG. 5*b* which may be of varying size, shape, and dimension.

Figure 6A:
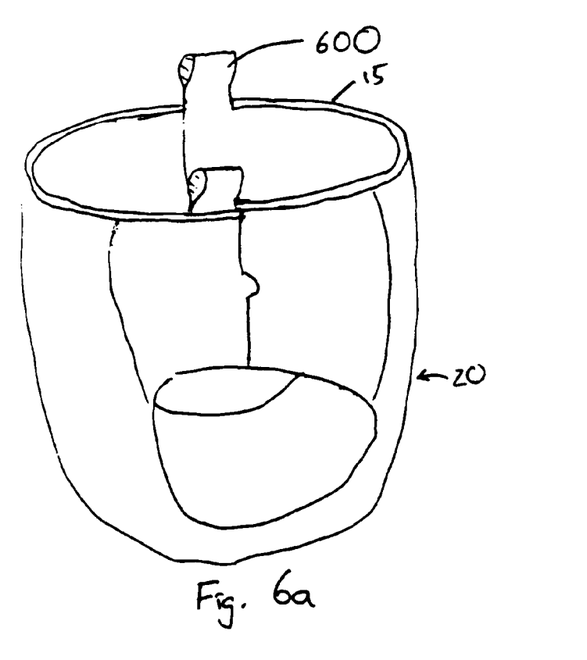
FIG. 6a is a perspective view of an absorbent article of the present invention having the handle as a loop.

FIG. 6*a* is a perspective view of another embodiment of the handle as a loop 600. FIG. 6*a* illustrates a preferred embodiment wherein dual loops extend from approximately the midpoint of the sidewalls. In one embodiment, the loop 600 is formed from a unitary tongue of material comprising the belt zone extending beyond the waist edge 15. The tongue is folded back onto itself, and the distal edge of the tongue is affixed to itself or to the garment-facing or wearer-facing surface of any lamina within the pull-on and in proximity to the waist edge 15. The resulting appendage is a loop 600 that may be grasped while applying the article. In an alternate embodiment, the loop 600 is formed from a discrete piece of woven, nonwoven, foam, or polymeric film material. The distal ends of the piece are welded to form the loop. The connected ends of the loop are affixed to the article, preferably interposed between two layers within the belt zone and at the waist edge 15. Alternately, the welding of the distal ends of the strip and the affixation of the strip to the article may be performed in a single step by any welding means known in the art. Additionally, the discrete loop may be affixed to the garment-facing surface of the article at any place such that the loop may be engaged by the wearer and is not limited to within the sidewall and at the waist edge 15.

In another embodiment, a single loop may extend from the waist edge 15 and within the back region of the chassis. Placement of such a loop will assist the wearer or caregiver in executing the finish.

In another embodiment, the loop 600 may be a stratum of material, ideally a laminated nonwoven similar in construction to the backsheet, partially welded to the garment-facing surface of the pull-on 20. The stratum is preferably welded at opposing ends with a nonwelded portion therebetween such that a loop is formed between the stratum and the backsheet. The resulting loop would resemble a "belt loop" as found on traditional garments such as pants.

Alternatively, the loop may comprise a string, thread, yarn, twine, or the like. In such an embodiment, the loop may be comprised of a natural or synthetic fiber. The string may furthermore be circumferentially interposed and optionally affixed between two laminae within the belt zone. At one or more points along the circumference of the waist edge 15, the string may protrude from the waist edge 15 to form a loop.

Figures 7A, 7B:
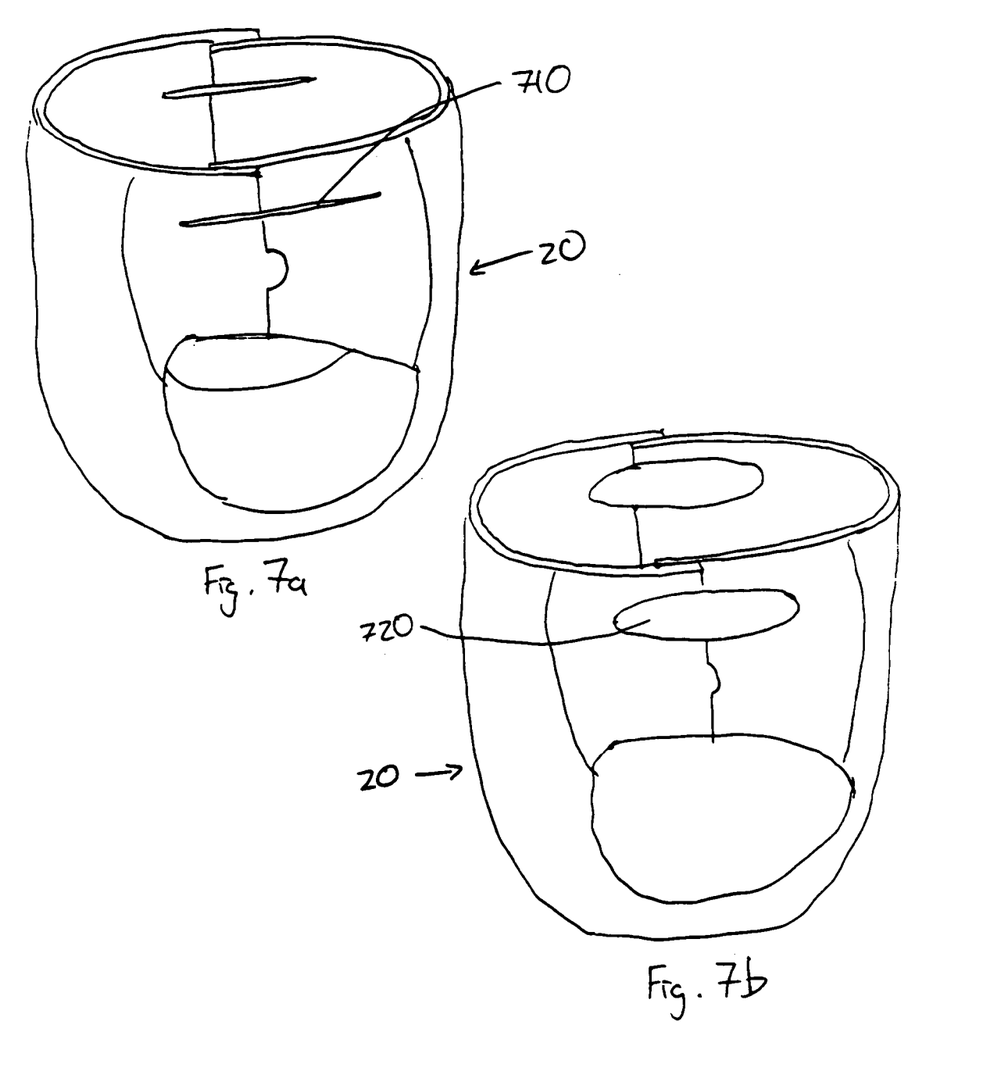
FIG. 7a is a perspective view of an absorbent article of the present invention having the handle as an aperture within the article.
FIG. 7b is a perspective view of an absorbent article of the present invention having the handle as an aperture comprising a distinct hole.

FIG. 7*a* is a perspective view of another embodiment of the handle as an aperture within the article. In a preferred embodiment, the aperture is within the belt zone. The aperture most preferably is a slit 710 through the sidewall such that the wearer can insert his or her fingers through the sidewall and grasp a portion of the belt zone. Most preferably, the slit is linear and substantially parallel to the waist edge 15. The sidewall region above the slit (adjacent to the waist edge 15) is then grasped by the wearer and used to apply the article.

The aperture can comprise a distinct hole 720 through the article as shown in FIG. 7*b*. A distinct hole 720 is an aperture wherein the void created has a non-negligible area. Such a hole would operate in a manner similar to a slit while being more conspicuous to the wearer. The hole is preferably elliptical; however, shape is not limiting.

The dimensions of the aperture are of an effective size such that a wearer can engage the aperture with his or her fingers. The dimensions of the aperture are limited only such that the article maintains a comfortable fit and functionality. While the aperture is ideally located on or along the sidewall and adjacent to the belt zone, one skilled in the art would recognize that the aperture may be located anywhere in the article so long as the aperture may be engaged by the wearer and the functional character of the article is not destroyed. Furthermore, the aperture may span the width of the sidewall such that the aperture is defined by the sidewall along two opposing edges and by the chassis on the other two opposing edges.

Further embodiments may result from the combination of any of the aforementioned handles. For example, an article may comprise a handle as a tab with the tab itself further comprising a grippable region. Use of one or more different handle embodiments within a single absorbent article is within the scope of this invention. For example, an article may comprise a grippable region and a loop.

In another embodiment of the present invention, the absorbent article may take the form of a training pant. A training pant is worn by an infant during a toilet training regimen. The toilet training regimen refers generally to the process whereby a caregiver transitions a diaper wearing infant to become self-sufficient in disposing of bodily waste by use of the toilet. The training pant provides a milestone for an infant who is developing an independence from the caregiver. A training pant must allow the child to raise and lower the garment without requiring the aid of a parent while still providing liquid and solid absorbency and preventing waste leakage. In a preferred embodiment, the training pant is provided to a caregiver. Preferably, the training pant is provided in packaging offering a plurality of pants to the caregiver. Within the packing, an instruction is provided for the caregiver. The instruction include instructions, guidance, counseling, strategies, and any verbal or non-verbal teachings (including graphical representations) provided to the caregiver regarding the toilet training regimen of the infant. Preferably, the instruction discloses a suggested method that a caregiver may use in transitioning the infant away from diaper use and toward toilet use. At least part of the instruction describes the use of the training pants of the present application as a transitioning tool in training.

For example, an exemplary instruction may define a timely progression from diapers to training pants to a traditional nonabsorbent undergarment divided into three phases. The phases need not necessarily be sequential and may, given the unique needs of any given infant, be intermittent or omitted. Furthermore, the phase may not be discrete; one or more phase may overlap another phase. In one phase, the infant is gradually introduced to the training pant by initial application and increased wear time of the training pant. The wear time of the pant is increased throughout the phase such that an infant begins the phase wearing a diaper almost exclusively and continuously and ends the phase wearing the training pant almost exclusively and continuously. During this phase, proper application of the training pant is taught by the caregiver. Preferably, the teaching will highlight the use of the handles. In particular, the handles should be emphasized for assisting in application and achieving proper fit. The teaching may also include that the handles should be employed when removing the training pant from its packaging and when unfurling the training pant prior to application. In another phase, the infant is gradually introduced to a traditional nonabsorbent undergarment by initial application and increased wear time of the undergarment. The wear time of the undergarment is increased throughout the phase such that an infant begins the phase wearing a training pant almost exclusively and continuously and ends the phase wearing the undergarment almost exclusively and continuously. In yet another phase, the infant is taught by the caregiver to use the toilet instead of soiling the garment worn by the infant. A caregiver utilizes a variety of behavioral modifications to achieve the goal of toilet use by the infant for urination and bowel movements. Behavioral modifications may involve using a "potty seat" (e.g., a child-sized self-contained portable toilet, a child-sized seat applied to a toilet, etc.), periodically setting the infant on the toilet, demonstrating the use of the toilet, reminding the infant to use the toilet, rewarding the infant for using the toilet including verbal praise and affection, talking to the infant about toilet use, gentle re-education and correction if the infant soils him or herself, setting goals for the infant, providing other instructional material to the child such as books or audio/visuals, and combinations thereof. This phase is ideally partially concurrent with at least one of the proceeding two phases. Completion of this phase is achieved by the infant being relatively autonomous in the predominately exclusive use of the toilet for urination and bowel movements. Being relatively autonomous means that the infant recognizes when toilet use is necessary, can disrobe such that the toilet may be used, and can use the toilet. Predominately exclusive use of the toilet recognizes that, as with any training, an infant may forget, have accidents, or lapse into pre-toilet training behavior. Completion of this phase need not coincide with any of the previously mentioned phases.

In another embodiment of the present invention, an absorbent article comprising one or more of the handle embodiments previously presented may be packaged in a kit containing a plurality of the absorbent articles. The absorbent articles are positioned within the kit such that the handle is readily accessible. Readily accessible means that the handle is visible to the wearer or caregiver and that the handle may be grasped and used for removal of the absorbent article from the kit. The kit may require activation so that the article becomes accessible (e.g., opening of a lid, removal of a panel, etc.). In a preferred embodiment, the kit is defined by numerous absorbent articles bound together as an entity and covered by a thermoplastic film over wrap. A particularly preferred kit is represented in U.S. Pat. No. 5,934,470 issued to Bauer et al. on Aug. 10, 1999. This kit enables absorbent articles to be delivered to and purchased by a consumer while economizing space. The thermoplastic film cover ideally contains an opening means to allow removal of a portion of the thermoplastic film cover and access to the absorbent articles. A typical opening means includes a substantially continuous line of weakness, preferably perforations within the thermoplastic film cover. An exemplary opening means is presented in U.S. Pat. No. 5,036,978 issued to Frank et al. on Aug. 6, 1991.

Upon activation of the opening means, the absorbent articles may be presented individually or multiply for removal from the kit. Regardless of such presentation, the handle will be visible and graspable. The handle may be presented by the manner in which the kit is opened. The handle may be presented in a manner in which the article is folded and/or stacked within the kit. The handle may be presented by the mere size, shape, or position of the handle. Typically, absorbent articles are positioned in a uniform manner within the kit (i.e., the articles are folded similarly and bound uniformly) with the waist edge being presented. In such a case, a handle as a tab along the waist edge would be readily accessible to a wearer or caregiver. The tab may be grasped and used to remove the article from the kits. Subsequently, a second article containing a tab would be presented from the kit.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changed and modification can be made without departing from the spirit and scope of the invention. It is therefore intended to cover in the appended claims all such changed and modifications that are within the scope of this invention.

What is claimed is:

1. An absorbent article having a front region, a back region, a belt zone extending circumferentially about the absorbent article, a wearer-facing surface, and a garment-facing surface: said absorbent article comprising:
   a) a chassis;
   b) at least one sidewall adjacently disposed to the chassis and connecting the front region to the back region thereby forming a leg opening and a waist edge; said sidewall comprising an ear or a panel, and
   c) at least one handle for assisting in the application of the article onto a wearer; wherein the handle is a flap comprising a stratum, wherein the flap forms a gap between the stratum and the chassis or sidewall, wherein said flap is joined to the garment-facing surface of the article by opposing longitudinal welds disposed proximate to opposing distal longitudinal edges of the flap, wherein the handle is disposed adjacent to either the chassis or sidewall and wherein the absorbent article is a pull-on garment.

2. The absorbent article of claim 1 wherein the chassis further comprises a liquid pervious topsheet, a liquid impervious backsheet joined with the topsheet, and an absorbent core interposed between the topsheet and backsheet.

3. The absorbent article of claim 2 wherein the backsheet further comprises at least a nonwoven outer cover.

4. The absorbent article of claim 1 wherein the flap comprises a unitary construction; wherein said stratum is a portion of the belt zone that has been folded away from the wearer-facing surface of the article at a hingepoint.

5. The absorbent article of claim 4 wherein said stratum comprises a cut through a portion of the stratum, wherein said cut is disposed along the waist edge.

6. The absorbent article of claim 4 wherein said stratum is joined to the garment-facing surface of the article by a lateral weld disposed substantially laterally and in proximity to the waist edge.

7. The absorbent article of claim 1 wherein the flap comprises a multiple construction; wherein said stratum is discrete.

8. The absorbent article of claim 7 wherein said stratum is joined to the garment-facing surface of the article by a lateral weld disposed substantially laterally and in proximity to the waist edge.

9. The absorbent article of claim 1 wherein said flap has a lateral width and a longitudinal length, wherein said lateral width is greater than the longitudinal length.

10. The absorbent article of claim 1 wherein the handle is disposed adjacent to the sidewall.

11. The absorbent article of claim 10 wherein the sidewall has a width and wherein the handle laterally spans said width of the sidewall.

12. The absorbent article of claim 1 wherein the sidewall comprises a single ear or panel.

13. The absorbent article of claim 1 wherein the sidewall comprises more than one ear or panel, wherein said ears or panels are connected to each other by a welding means selected from a group consisting of sonic sealing, heat sealing, pressure bonding, adhesive or cohesive bonding, sewing, and autogeneous bonding.

14. A kit for toilet training an infant comprising:
 a) the article of claim 1 in the form of a training pant and
 b) an instruction to a caregiver for transitioning the infant to proper toilet use.

15. The kit of claim 14 wherein the instruction to the caregiver for transitioning the infant to proper toilet use includes use of the handle.

16. The kit of claim 14 wherein the instruction to the caregiver for transitioning the infant to proper toilet use includes description of a behavior modification.

17. A kit comprising more than one absorbent article of claim 1 wherein the article is positioned within said kit such that the handle is readily accessible.

18. A kit toilet training an infant comprising:
 a) a plurality of training pants having a front region, a back region, a belt zone extending circumferentially about the absorbent article, a wearer-facing surface, and a garment-facing surface; each said training pant comprising:
  i) a chassis;
  ii) at least one sidewall adjacently disposed to the chassis and connecting the front region to the back region thereby forming a leg opening and a waist edge; said sidewall comprising an ear or a panel, and
  iii) at least one handle for assisting in the application of the training pant onto a wearer; wherein the handle is a flap comprising a stratum, wherein the flap forms a gap between the stratum and the chassis or sidewall, said flap having a lateral width greater than the longitudinal length, wherein the lateral width is substantially parallel to the waist edge, wherein the handle is disposed adjacent to the sidewall;
 b) a thermoplastic film covering the plurality of training pants; and
 c) an instruction to a caregiver for transitioning the infant to proper toilet use.

* * * * *